(12) United States Patent
Rodden et al.

(10) Patent No.: US 6,297,348 B1
(45) Date of Patent: Oct. 2, 2001

(54) CLOSELY LINKING A NDA PROCESS WITH A PEN PROCESS

(75) Inventors: John Bernard Rodden, Houston, TX (US); Glenn William Elliott, Akron, OH (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/644,454

(22) Filed: Aug. 22, 2000

Related U.S. Application Data

(60) Provisional application No. 60/151,603, filed on Aug. 30, 1999, provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,606, filed on Aug. 30, 1999, provisional application No. 60/151,589, filed on Aug. 30, 1999, provisional application No. 60/151,497, filed on Aug. 30, 1999, provisional application No. 60/151,590, filed on Aug. 30, 1999, and provisional application No. 60/151,578, filed on Aug. 30, 1999.

(51) Int. Cl.[7] .......................... C08G 63/18; C07C 69/70

(52) U.S. Cl. .......................... 528/298; 528/308; 528/499; 528/500; 528/501; 560/76; 560/77; 560/100

(58) Field of Search ...................... 528/298, 308, 528/499, 500, 501; 560/76, 77, 100

(56) References Cited

U.S. PATENT DOCUMENTS 4,755,587  7/1988  Rinehart ............................. 528/272

*Primary Examiner*—Samuel A. Acquah

(57) ABSTRACT

Disclosed is a method for closely linking a process for producing 2,6-naphthalene dicarboxylic acid (2,6-NDA) with a process for producing polyethylene naphthalate, thus eliminating the need for drying 2,6-NDA, handling solid 2,6-NDA, and optimizing particle size of 2,6-NDA which comprises:

a) Adding an aqueous slurry of polymer grade 2,6-NDA directly into a process for making PEN, either by directly adding a stream from a 2,6 NDA process into a PEN process, or by adding water to polymer grade 2-6-NDA prior to adding the resulting slurry to a PEN process.

b) Removing the slurry water during the first esterification reaction at the same time the water of reaction is removed.

7 Claims, No Drawings

CLOSELY LINKING A NDA PROCESS WITH A PEN PROCESS

CROSS REFERENCES

This application claims the benefit of U.S. Provisional Application No. 60/151,603, filed Aug. 30, 1999, the entire disclosure of which is hereby incorporated by reference This application is related to U.S. application Ser. Nos. 60/151,577, 60/151,607, 60/151,498, 60/151,602, 60/151,529, 60/151,489, 60/151,604, 60/151,606, 60/151,589, 60/151,497, 60/151,590, and 60/151,578, filed of even date.

FIELD OF INVENTION

This invention relates to the production of 2,6-naphthalene dicarboxylic acid (hereinafter abbreviated as 2,6-NDA) and to the production of polyethylene naphthalate (hereinafter abbreviated as PEN). More particularly this invention makes it possible for the first time to eliminate the drying and solids handling portions of a process for preparing 2,6-NDA and pump the 2,6-NDA in an aqueous slurry directly into to a process for making PEN. This invention also relates to the preparation of 2,6- NDA pure enough for polymerization.

BACKGROUND OF THE INVENTION

Films, fibers and other shaped articles prepared from PEN display improved strength and thermal properties relative to other polyester materials. High strength fibers made from PEN can be used to make tire cords and films made from PEN are advantageously used to manufacture magnetic recording tape and components for electronic applications. In comparison with polyethylene terephthalate, PEN is excellent, for example, in mechanical strength and heat stability. PEN is used for films for magnetic tapes, for films for packaging, and for condensers. In recent years it has been used for photograph supports because of its dimensional stability in the form of a thin film.

2,6-NDA and ethylene glycol are the raw materials for producing PEN. The methods for producing PEN are the esterification process and the direct polymerization process, each of which can be carried out batchwise or continuously. Currently in the art the esterification process is more commonly used, but usually employs as the raw material a salt of 2,6-NDA, 2,6-naphthalene dicarboxylate (hereinafter abbreviated 2,6-NDC). 2,6-NDC is often in crystal form with impurities trapped in the structure. 2,6-NDC is used, because there have been no processes available in the art to produce polymerization grade 2,6-NDA, the preferred monomer for making PEN. The availability of a process for making polymer grade 2,6-NDA would make it possible to pursue the preferred route to PEN. This would represent a revolutionary advance in the art. PEN produced by such a process would be much more economical.

It is also known in the art that all previous processes for producing NDA and NDC deliver a solid product that is usually shipped to the polymer manufacturing plant. Though 2,6-NDA is the preferred monomer, handling of NDA particles is still difficult and expensive. In addition, particle size can be critical where dry handling of solids is practiced.

U.S. Ser. No. 4,755,587, for example, discusses the problem of handling solids and claims advantages using very small porous pellets.

Copending U.S. Ser. No. 60/151,577, filed of even date, and incorporated by reference herein in its entirety, discloses a process for producing 2,6-NDA of polymer grade. The new process is unique in many respects. Of particular importance, the new process can operate using relatively impure methylnaphthalene feedstock with respect to organic hydrocarbon impurities, allows for debromination of the oxidation product in the liquid phase, and avoids the isolation of purified naphthoic acid.

The advent of a process for making polymer grade 2,6-NDA, suitable for direct use in a PEN process without esterification, or solids drying and handling and the associated problems of particle size control is of tremendous value in the art. Such a process constitutes a very significant advance in the art, is much more economical, and is capable of producing polymer grade 2,6-NDA that could be slurried directly into a PEN process. This eliminates problems with solids handling, including the major expense of transporting the 2,6-naphthalene dicarboxylate solids. This constitutes a tremendous advance in the art.

SUMMARY

In accordance with the foregoing the present invention is a process for close coupling of a process for making 2,6-NDA and a process for making PEN that has not previously been possible in the art. The invention comprises directly pumping an aqueous slurry of 2,6-NDA, generated in a process for producing 2,6 NDA, into a process for producing PEN. Alternatively, the invention also comprises adding water to 2,6-NDA of polymer quality, which may or may not be already wetted with water, and pumping the resulting slurry of 2,6-NDA directly into a process for producing PEN.

The process comprises:
Pumping an aqueous slurry of polymer grade 2,6-NDA directly into a process for making PEN, either by directly pumping a stream from a 2,6 NDA process into a PEN process, or by adding water to polymer grade 2-6-NDA prior to pumping the resulting slurry to the PEN process.
Removing the slurry water during the first esterification reaction at the same time the water produced by the esterification reaction is removed.

The following advantages are realized by the disclosed process:
The process allows for the elimination of costly drying equipment that would otherwise be associated with the final steps of the 2-6 NDA process. Through the invention, equipment typically required in the PEN process, such as dense phase or paste make-up facilities, is also eliminated.
Through the inclusion of additional water in the first stage of esterification, the final PEN product is expected to be very low in diethylene glycol concentration. Diethylene glycol is a known contaminant in PEN.

DETAILED DESCRIPTION OF THE INVENTION

In the process of the present invention, the 2,6-NDA is a grade that can be used directly in polymerization of PEN. Previously in the art there has not been any process to produce 2,6-NDA monomer of this purity through the use of a final aqueous purification step which uses a reasonable amount of water at moderate temperature and pressure conditions. However, copending U.S. Ser. No. 60/151,577 claims an integrated process for producing 2,6-NDA of the requisite quality and purity which comprises:
a) Reacting a hydrocarbon stream containing predominantly methylnaphthalene with an oxygen-containing gas in the presence of a suitable solvent and catalyst to form a crude mixture of naphthoic acid (crude product NA), wherein said crude product NA remains dissolved in the solvent;

b) Recovering said crude product NA by evaporation of solvent and washing said crude product NA with water;

c) Debrominating said crude product NA by passing over a supported catalyst in the presence of hydrogen, and water-washing said crude debrominated product NA;

d) Contacting said crude, debrominated product NA with an aqueous base of potassium to extract pure NA as the aqueous potassium salt of NA;

e) Separating said aqueous potassium salt of NA from the remaining organic liquid (containing methylnaphthalene and partially oxidized reaction intermediates), and recycling said organic liquid to step a);

f) Contacting said aqueous potassium salt of NA with naphthalene vapor, adding a solid catalyst, and removing water by evaporation to form a slurry of solid potassium salt of NA and catalyst suspended in liquid naphthalene;

g) Reacting said slurry in the presence of carbon dioxide to convert solid potassium salt of NA to liquid naphthalene and solid dipotassium salt of 2,6-NDA(2,6-K2NDA);

h) Reducing the pressure to vaporize the naphthalene, and separating the solids from the naphthalene vapor by a novel separation using cyclones, recycling a portion of the naphthalene to step (f), and recovering the remainder as a product, or methylating the naphthalene via direct alkylation or transalkylation to provide additional methylnaphthalene feed for step (a);

i) Contacting the solids with water to create a mixture of aqueous potassium salts (comprising the potassium salt of NA, KNA, and the dipotassium salt of 2,6-NDA, 2,6-K2NDA, and its isomers) and solid catalyst;

j) Separating the solid catalyst from the mixture of aqueous potassium salts and recycling it to step (f);

k) Adding aqueous potassium bicarbonate to the mixture of aqueous potassium salts and evaporating a portion of the water to selectively crystallize the dipotassium salt of 2,6-NDA as a solid, separating said solid, and recycling the remaining liquid to step (d);

l) Dissolving the solid dipotassium salt of 2,6-NDA in water;

m) Optionally passing said aqueous dipotassium salt of 2,6-NDA through an activated carbon bed to remove impurities;

n) Contacting said aqueous dipotassium salt of 2,6-NDA with carbon dioxide to create a mixture of solid monopotassium salt of 2,6-NDA and aqueous potassium bicarbonate, separating said solids, and recycling the aqueous potassium bicarbonate to step (k);

o) Contacting solid monopotassium salt of 2,6-NDA with water, optionally in the presence of carbon dioxide, to form solid 2,6-NDA, aqueous dipotassium salt of 2,6-NDA, and potassium bicarbonate;

p) Separating the solid 2,6-NDA and recycling the liquid containing aqueous dipotassium salt of 2,6-NDA and potassium bicarbonate to step (n);

q) Contacting solid 2,6-NDA with water in a pipe reactor to remove traces of potassium ion impurity;

r) Separating solid 2,6-NDA and recycling water to step q).

Copending U. S. Ser. No. 60/151,577 offers a very efficient integrated process for producing the preferred 2,6 NDA from inexpensive olefin plant and refinery feedstock and demonstrates a number of novel aspects and advantages over any process available in the art. The process allows oxidation of crude methylnaphthalene feed, and includes improved oxidation product purification steps, including a novel hydrodebromination step, and eliminates the need to isolate a pure acid intermediate. The invention incorporates a disproportionation step, followed by new steps in separation and purification of the disproportionation product, and also demonstrates very efficient potassium recycle. Optionally, the process allows for efficient recycle of the reaction co-product and conversion into additional methylnaphthalene feed.

Methylnapthalene is fed into an oxidation reactor. For most commercial feedstock sources, the methylnaphthalene will be a mixture of two isomers, 1-methylnaphthalene and 2-methylnaphthalene. The methylnaphthalene is oxidized to a mixture of the corresponding isomers of naphthoic acid in the presence of a catalyst comprising Co, Mn and Br. The resulting crude product naphthoic acid remains in the liquid phase. The mixture of isomers of napthoic acid are recovered by an evaporative distillation which removes acetic acid, and subsequently washed with water to remove inorganic Br, phthalic acid, trimellitic acid and Co/Mn. The crude product naphthoic acid is hydrodebrominated by passing the crude product NA over a catalyst comprising palladium on carbon, the debromination taking place in the absence of solvents. The debrominated crude product NA is then washed again with water to remove residual inorganic bromine.

The crude, debrominated naphthoic acid is reacted with basic potassium in 0–50% molar excess at a temperature of about 100° C. to form a concentrated solution of the dipotassium salt of the acid and to drive off carbon dioxide. The dipotassium salt of naphthoic acid and said by-products are separated. The naphthalene by-products are recycled back to the oxidation reactor. Water is added to the dipotassium salt of naphthoic acid and the aqueous solution is pumped into a reactor where water is evaporated.

The aqueous solution is then contacted with hot napthalene and the aqueous solution of salts and naphthalene is introduced into a reactor as a slurry to which has been added a catalyst comprising ZnO in an amount of about 5–20% by weight.

The naphthalene slurry containing particulate salts and ZnO catalyst is reacted in a disproportionation reactor to produce 2,6-K2NDA. The disproportionation step is optionally, and preferably, repeated in a second disproportionation reactor to improve yields.

After disproportionation the napthalene is flashed from the reaction product. The flashed naphthalene is heated and recycled for use in the evaporation of water from potassium salt, and for use as a diluent for potassium salt as it enters the disproportionation reactor. The solid product consisting of K2NDA isomers is washed and the liquid is filtered to remove catalyst and coke particles.

The liquid carrying mixed organic salts is introduced into a two-stage evaporative crystallization section where the K2NDA is selectively precipitated, the $KHCO_3$ is recycled, and the purified K2NDA is redissolved with additional $H_2O$. Then the purified K2NDA is passed through an activated carbon bed.

Next, the monopotassium salt of 2,6-NDA, (KHNDA) is selectively precipitated and the KHNDA solids are disproportionated into 2,6-NDA and K2NDA. The product of disproportionation is centrifuged to yield a 2,6 NDA slurry, and a centrate containing predominantly 2,6 K2NDA and KHCO$_3$. Residual potassium is removed by passing the 2,6 NDA through a pipe reactor and washing the 2,6-NDA in water at about 150° C. The process results in solid 2,6-NDA product in a water slurry.

In the process of the present invention, the solid 2,6-NDA produces by the process of copending 60/151,577 or any others which may be discovered in the future which provide polymer grade monomer is not separated as a solid, but is retained in a water slurry following purification. For example, when coupled with the process disclosed in copending U.S. application Ser. No. 60/151,577 and U.S. application Ser. No. 60/151,602 also incorporated by reference herein in the entirety, the final centrifuge and subsequent drying steps required to produce dry solid 2,6-NDA are eliminated by the present invention.

We claim:

1. A process for closely linking a process for producing 2,6-naphthalene dicarboxylic acid(2,6-NDA) with a process for producing polyethylene naphthalate which eliminates need for drying 2,6-NDA, handling solid 2,6-NDA, and optimizing particle size of 2,6-NDA which comprises:

Pumping an aqueous slurry of polymer grade 2,6-NDA directly into a process for making PEN, either by directly pumping a stream from a 2,6 NDA process into a PEN process, or by adding water to polymer grade 2-6-NDA prior to pumping the resulting slurry to the PEN process, b) Removing the slurry water during the first esterification reaction at the same time the water of reaction is removed.

2. The process of claim 1 further comprising the esterification reaction taking place in an esterification reactor designed to accommodate additional water.

3. The process of claim 1 further comprising removing a portion of the water in the slurrry in pre-evaporator prior to the esterification reaction.

4. The process of claim 1 wherein polymer grade 2,6-NDA is produced by:

a) Reacting a hydrocarbon stream containing predominantly methylnaphthalene with an oxygen-containing gas in the presence of a suitable solvent and catalyst to form a crude mixture of naphthoic acid (crude product NA), wherein said crude product NA remains dissolved in the solvent;

b) Recovering said crude product NA by evaporation of solvent and washing said crude product NA with water;

c) Debrominating said crude product NA by passing over a supported catalyst in the presence of hydrogen, and water-washing said crude debrominated product NA;

d) Contacting said crude, debrominated product NA with an aqueous base of potassium to extract pure NA as the aqueous potassium salt of NA;

e) Separating said aqueous potassium salt of NA from the remaining organic liquid (containing methylnaphthalene and partially oxidized reaction intermediates), and recycling said organic liquid to step a);

f) Contacting said aqueous potassium salt of NA with naphthalene vapor, adding a solid catalyst, and removing water by evaporation to form a slurry of solid potassium salt of NA and catalyst suspended in liquid naphthalene;

g) Reacting said slurry in the presence of carbon dioxide to convert solid potassium salt of NA to liquid naphthalene and solid dipotassium salt of 2,6-NDA(2,6-K2NDA);

h) Reducing the pressure to vaporize the naphthalene, and separating the solids from the naphthalene vapor by a novel separation using cyclones, recycling a portion of the naphthalene to step (f), and recovering the remainder as a product, or methylating the naphthalene via direct alkylation or transalkylation to provide additional methylnaphthalene feed for step (a);

i) Contacting the solids with water to create a mixture of aqueous potassium salts (comprising the potassium salt of NA, KNA, and the dipotassium salt of 2,6-NDA, 2,6-K2NDA, and its isomers) and solid catalyst;

j) Separating the solid catalyst from the mixture of aqueous potassium salts and recycling it to step (f);

k) Adding aqueous potassium bicarbonate to the mixture of aqueous potassium salts and evaporating a portion of the water to selectively crystallize the dipotassium salt of 2,6-NDA as a solid, separating said solid, and recycling the remaining liquid to step (d);

l) Dissolving the solid dipotassium salt of 2,6-NDA in water;

m) Optionally passing said aqueous dipotassium salt of 2,6-NDA through an activated carbon bed to remove impurities;

n) Contacting said aqueous dipotassium salt of 2,6-NDA with carbon dioxide to create a mixture of solid monopotassium salt of 2,6-NDA and aqueous potassium bicarbonate, separating said solids, and recycling the aqueous potassium bicarbonate to step (k);

o) Contacting solid monopotassium salt of 2,6-NDA with water, optionally in the presence of carbon dioxide, to form solid 2,6-NDA, aqueous dipotassium salt of 2,6-NDA, and potassium bicarbonate;

p) Separating the solid 2,6-NDA and recycling the liquid containing aqueous dipotassium salt of 2,6-NDA and potassium bicarbonate to step (n);

q) Contacting solid 2,6-NDA with water in a pipe reactor to remove traces of potassium ion impurity;

r) Separating solid 2,6-NDA and recycling water to step o)

s) Washing the solid 2,6 NDA with additional water t) Separating the water from the solid, producing wet polymer grade 2,6 NDA, and recycling most of the water to step q)

u) Drying the solid 2-6 NDA.

5. The process of claim 1 wherein the polymer grade 2,6-NDA is made by any process that produces polymer grade 2,6-NDA.

6. In a process for producing polyethylene naphthalate from 2,6-naphthalene dicarboxylic acid, an improvement which avoids the need for handling dry solid 2,6-naphthalene dicarboxylic acid and derivatives thereof which comprises:

a) Reacting a hydrocarbon stream containing predominantly methylnaphthalene with an oxygen-containing gas in the presence of a suitable solvent and catalyst to form a crude mixture of naphthoic acid (crude product NA), wherein said crude product NA remains dissolved in the solvent;

b) Recovering said crude product NA by evaporation of solvent and washing said crude product NA with water;

c) Debrominating said crude product NA by passing over a supported catalyst in the presence of hydrogen, and water-washing said crude debrominated product NA;

d) Contacting said crude, debrominated product NA with an aqueous base of potassium to extract pure NA as the aqueous potassium salt of NA;

e) Separating said aqueous potassium salt of NA from the remaining organic liquid (containing methylnaphthalene and partially oxidized reaction intermediates), and recycling said organic liquid to step a);
f) Contacting said aqueous potassium salt of NA with naphthalene vapor, adding a solid catalyst, and removing water by evaporation to form a slurry of solid potassium salt of NA and catalyst suspended in liquid naphthalene;
g) Reacting said slurry in the presence of carbon dioxide to convert solid potassium salt of NA to liquid naphthalene and solid dipotassium salt of 2,6-NDA(2,6-K2NDA);
h) Reducing the pressure to vaporize the naphthalene, and separating the solids from the naphthalene vapor by a novel separation using cyclones, recycling a portion of the naphthalene to step (f), and recovering the remainder as a product, or methylating the naphthalene via direct alkylation or transalkylation to provide additional methylnaphthalene feed for step (a);
i) Contacting the solids with water to create a mixture of aqueous potassium salts (comprising the potassium salt of NA, KNA, and the dipotassium salt of 2,6-NDA, 2,6-K2NDA, and its isomers) and solid catalyst;
j) Separating the solid catalyst from the mixture of aqueous potassium salts and recycling it to step (f);
k) Adding aqueous potassium bicarbonate to the mixture of aqueous potassium salts and evaporating a portion of the water to selectively crystallize the dipotassium salt of 2,6-NDA as a solid, separating said solid, and recycling the remaining liquid to step (d);
l) Dissolving the solid dipotassium salt of 2,6-NDA in water;
m) Optionally passing said aqueous dipotassium salt of 2,6-NDA through an activated carbon bed to remove impurities;
n) Contacting said aqueous dipotassium salt of 2,6-NDA with carbon dioxide to create a mixture of solid monopotassium salt of 2,6-NDA and aqueous potassium bicarbonate, separating said solids, and recycling the aqueous potassium bicarbonate to step (k);
o) Contacting solid monopotassium salt of 2,6-NDA with water, optionally in the presence of carbon dioxide, to form solid 2,6-NDA, aqueous dipotassium salt of 2,6-NDA, and potassium bicarbonate;
p) Separating the solid 2,6-NDA and recycling the liquid containing aqueous dipotassium salt of 2,6-NDA and potassium bicarbonate to step (n);
q) Contacting solid 2,6-NDA with water in a pipe reactor to remove traces of potassium ion impurity;
r) Separating solid 2,6-NDA and recycling water to step o)
s) Washing the solid 2,6 NDA with additional water
t) Performing a crude separation of the water from the solid, producing wet polymer grade 2,6 NDA, and recycling most of the water to step q)
u) Adding water to the wet polymer grade 2,6-NDA to form a pumpable slurry,
v) Pumping the aqueous slurry directly into a process for making PEN,
w) Removing the slurry water during the first esterification reaction at the same time the water of reaction is removed.

7. The process of claim 6 wherein steps t) and u) are eliminated.

* * * * *